US010385075B1

(12) United States Patent
Goodman et al.

(10) Patent No.: US 10,385,075 B1
(45) Date of Patent: Aug. 20, 2019

(54) MECHANOCHEMICAL FUNCTIONALIZATION OF SILICON

(71) Applicant: Nanostar Inc., New Orleans, LA (US)

(72) Inventors: Jonathan Goodman, Evanston, IL (US); Shiva Adireddy, Picayune, MS (US); Alexander L. Girau, Metairie, LA (US)

(73) Assignee: Nanostar, Inc., New Orleans, LA (US)

( * ) Notice: Subject to any disclaimer, the term of this patent is extended or adjusted under 35 U.S.C. 154(b) by 10 days.

(21) Appl. No.: 16/201,108

(22) Filed: Nov. 27, 2018

Related U.S. Application Data

(60) Provisional application No. 62/744,424, filed on Oct. 11, 2018.

(51) Int. Cl.
*C07F 7/08* (2006.01)
*C09C 1/28* (2006.01)

(52) U.S. Cl.
CPC .......... *C07F 7/0801* (2013.01); *C07F 7/0805* (2013.01); *C09C 1/28* (2013.01); *C01P 2002/76* (2013.01); *C01P 2002/82* (2013.01); *C01P 2004/03* (2013.01); *C01P 2004/04* (2013.01); *C01P 2004/62* (2013.01); *C01P 2004/64* (2013.01)

(58) Field of Classification Search
CPC ........ C07F 7/0801; C07F 7/0805; C09C 1/28; C01P 2002/76; C01P 2002/82; C01P 2004/03; C01P 2004/04; C01P 2004/62; C01P 2004/64
See application file for complete search history.

(56) References Cited

U.S. PATENT DOCUMENTS

| | | |
|---|---|---|
| 5,702,060 A | 12/1997 | Matteazzi et al. |
| 6,132,801 A | 10/2000 | Linford |
| 6,284,317 B1 | 9/2001 | Laibinis et al. |
| 6,444,009 B1 | 9/2002 | Liu et al. |
| 6,855,204 B2 | 2/2005 | Kauzlarich et al. |
| 7,371,666 B2 | 5/2008 | Swihart et al. |
| 7,531,155 B2 | 5/2009 | Li et al. |
| 7,790,316 B2 | 9/2010 | Aramata et al. |
| 7,883,995 B2 | 2/2011 | Mitchell et al. |
| 7,989,504 B2 | 8/2011 | Adam et al. |
| 9,461,304 B2 | 10/2016 | Newbound et al. |
| 9,461,309 B2 | 10/2016 | Newbound et al. |
| 9,608,262 B2 | 3/2017 | Aramata et al. |
| 9,650,536 B2 | 5/2017 | Ronne et al. |
| 9,765,271 B2 | 9/2017 | Myrick |
| 2005/0136330 A1 | 6/2005 | Mao et al. |
| 2005/0267345 A1 | 12/2005 | Korgel et al. |
| 2006/0167139 A1 | 7/2006 | Nelson et al. |
| 2008/0248307 A1 | 10/2008 | Jurbergs et al. |
| 2015/0243973 A1 | 8/2015 | Newbound et al. |
| 2015/0263342 A1 | 9/2015 | Newbound et al. |
| 2016/0164085 A1 | 6/2016 | Hanelt |
| 2017/0338476 A1 | 11/2017 | Newbound et al. |

OTHER PUBLICATIONS

Balaz, P., Mechanochemistry in Nanoscience and Minerals Engineering, High-Energy Milling, 2008, 103-132.
Cook, R.F., Strength and sharp contact fracture of silicon, J. Mater. Sci. 2006, 41, 841-872.
He, Y. et al. In situ observations of shear-driven amorphization in silicon crystals, Nature Nanotech. 2016, 11, 866-871.
Heintz, A.S., et al. Mechanochemical Synthesis of Blue Luminescent Alkyl/Alkenyl-Passivated Silicon Nanoparticles, Adv. Mat. 2007, 19, 3984-3988.
Huan, C., Shu-Qing, S., Silicon Nanoparticles: Preparation, properties, and applications, Chin. Phys. B, 2014, 23(8), 088102 1-14.
Kasukabe, T. et al. Beads-Milling of Waste Si Sawdust into High-Performance Nanoflakes for Lithium-Ion Batteries. Sci. Rep. 7, 42734.
Kuang, L., et al. Silicon nanoparticles synthesised through reactive high-energy ball milling: enhancement of optical properties from the removal of iron impurities, J. Exp. Nanosci. 2014.
Michalak, D. J., et al. Nanopatterning Si(111) surfaces as a selective surface-chemistry route, Nature Mat. 2010, 9, 266-271.
Nelles, J. et al. Functionalization of silicon nanoparticles via hydrosilylation with 1-alkenes, Colloid Polym. Sci., 2007, 285:729-736.
Su, X., et al. Mild Two-Step Method to Construct DNA-Conjugated Silicon Nanoparticles: Scaffolds for the Detection of MicroRNA-21, Bioconjugate Chem., 2014.
Verdoni, L.P., A fractionation process of mechanochemically synthesized blue-green luminescent alkyl-passivated silicon nanoparticles, Chem. Eng. J. 2011, 172, 591-600.
Xu, Z., et al. Water-soluble PEGylated silicon nanoparticles and their assembly into swellable nanoparticle aggregates,. J. Nanopart Res. 2015, 17:56.
Zhao, S. et al., Pressure and shear-induced amorphization of silicon, Extreme Mechanics Letters (2015).

*Primary Examiner* — Clinton A Brooks

(57) ABSTRACT

The mechanochemically functionalizing silicon nanoparticles and the functionalized silicon nanoparticles are described. The processes include applying shear forces to silicon metal the presence of an alkane and thereby functionalizing the silicon with an alkyl-functionalization. The resulting product includes a plurality of silicon nanoparticles each carrying an alkyl-functionalization derived from an alkane.

16 Claims, 4 Drawing Sheets

MECHANOCHEMICAL FUNCTIONALIZATION OF SILICON

CROSS-REFERENCE TO RELATED APPLICATIONS

This disclosure claims the benefit of priority to U.S. Application No. 62/744,424, filed 11 Oct. 2018, which is incorporated herein in its entirety.

FIELD OF THE INVENTION

Embodiments of the present invention generally relate to the mechanochemical modification of the surface of silicon metal.

BACKGROUND

Mechanochemical processes are those where an initial step in the chemical process is the breakage of atomic bonding by a function of mechanical force. While early studies on mechanochemical systems thought that the process was a conversion of mechanical into chemical energy, work developed since the 1960s has shown the nature of the process to be directly connected to the cleavage of chemical bonds and the rearrangement of the cleaved parts.

SUMMARY

A first embodiment is a process of mechanochemically functionalizing silicon nanoparticles with an alkane, the process can include repeatedly applying sufficient shear forces to silicon metal in the presence of an alkane thereby mechanochemically functionalizing the silicon and providing an alkyl-functionalization on the surface of the silicon; and continuing to apply the shear forces to the silicon in the presence of the alkane until the silicon metal is reduced to a plurality of functionalized silicon nanoparticles.

A second embodiment is a process that can include repeatedly applying sufficient shear forces to silicon metal in the presence of an admixture of an alkane and an alkene thereby mechanochemically functionalizing the silicon and providing a functionalization on the surface of the silicon; and continuing to apply the shear forces to the silicon in the presence of the alkane and the alkene until the silicon metal is reduced to a plurality of functionalized silicon nanoparticles.

A third embodiment is a process that includes shearing silicon metal thereby exposing a silicon surface having a Miller index other than a (111) plane or a (100) plane, the silicon surface carrying at least one silicon radical; where the silicon radical is of sufficient energy to react with an alkane; mechanochemically functionalizing the silicon surface by reacting the silicon radical with an organic coating agent, thereby covalently bonding the organic coating agent to the silicon surface.

A fourth embodiment is a material that can include a plurality of silicon nanoparticles each carrying an alkyl-functionalization derived from an alkane.

BRIEF DESCRIPTION OF THE FIGURES

For a more complete understanding of the disclosure, reference should be made to the following detailed description and accompanying drawing figures wherein.

Figure 1:
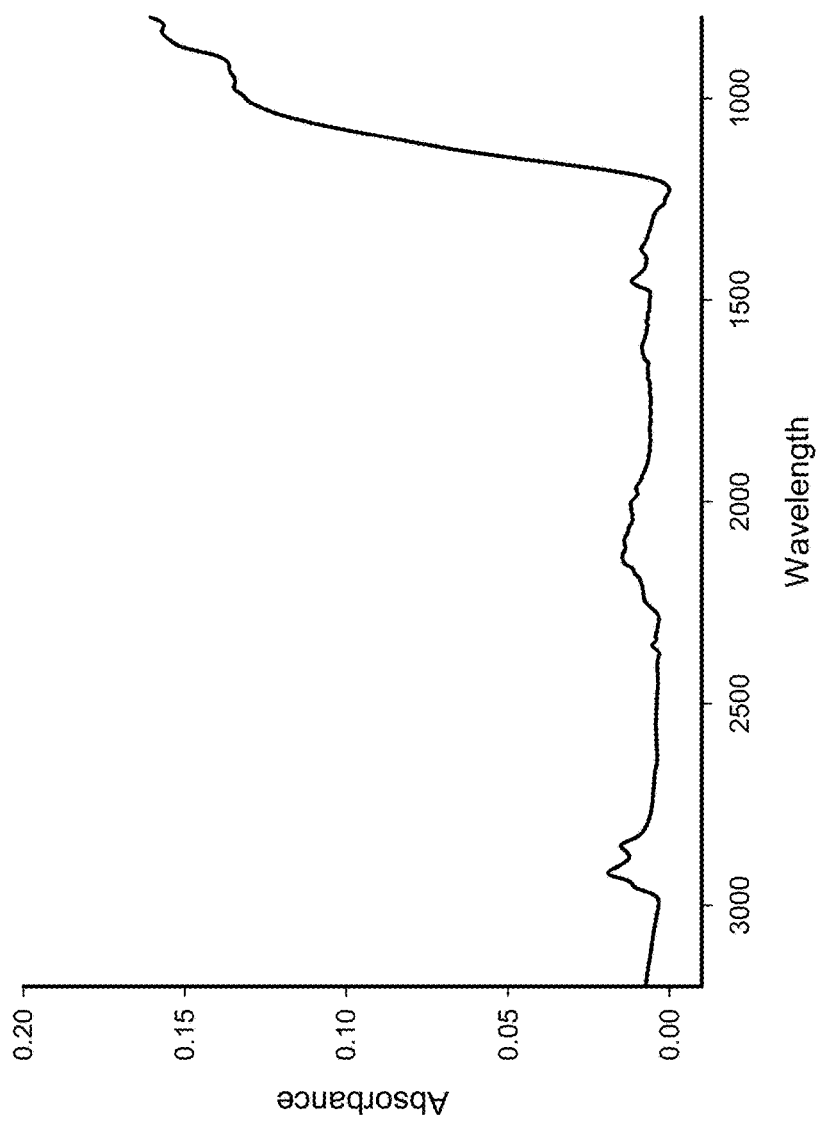
FIG. 1 is a plot of FTIR data from the product of the herein described shear process.
Figure 2:
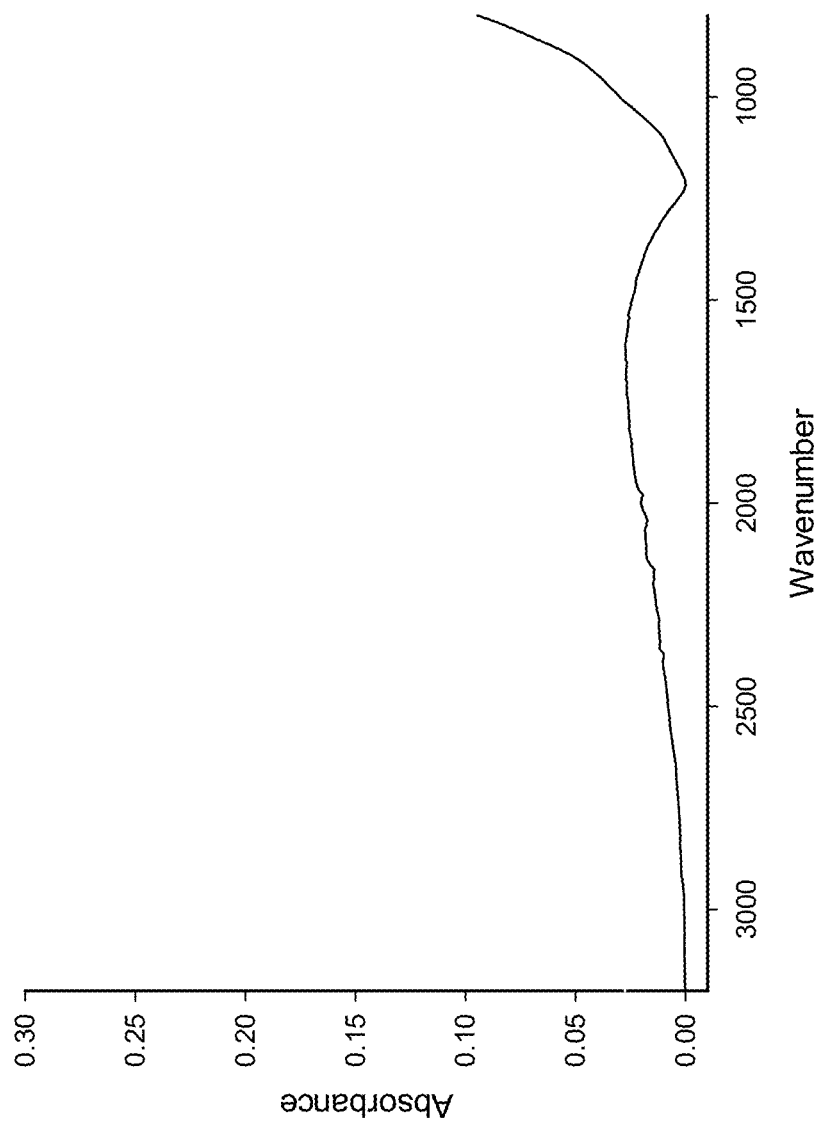
FIG. 2 is a comparative plot of FTIR data from an impact only system as described in U.S. Pat. No. 7,883,995.
Figure 3:
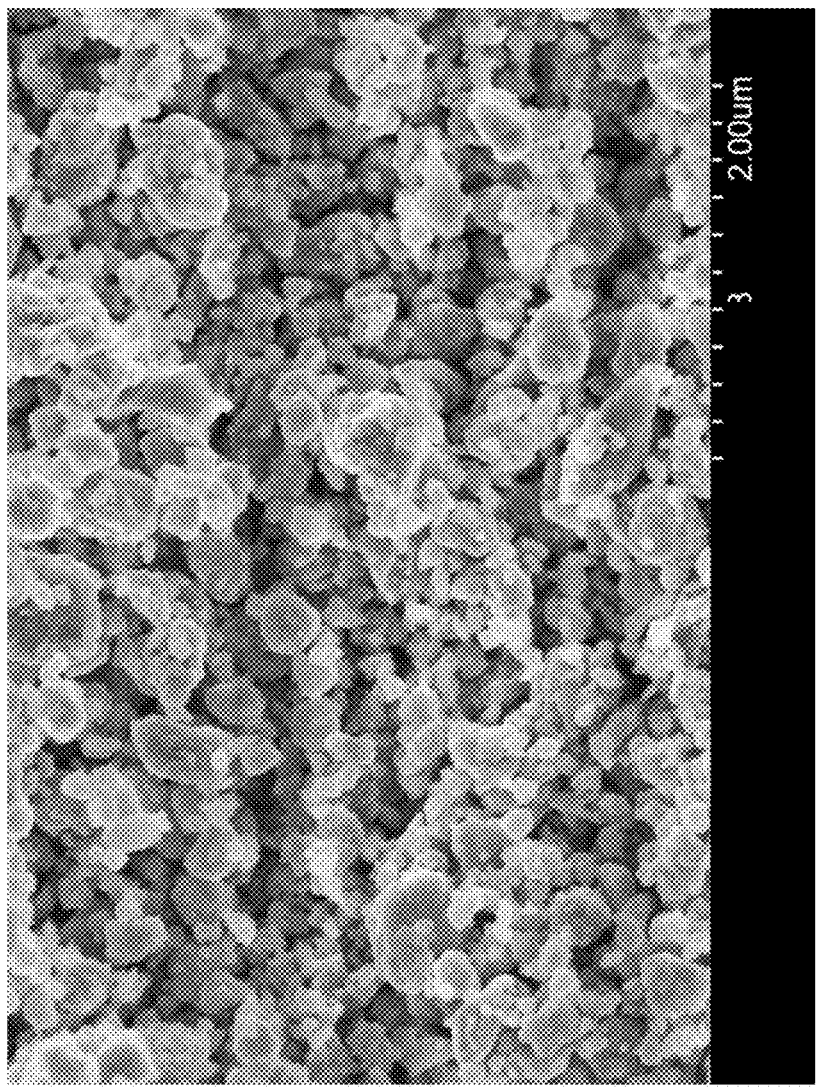
FIG. 3 is a SEM image of the herein disclosed product.
Figure 4:
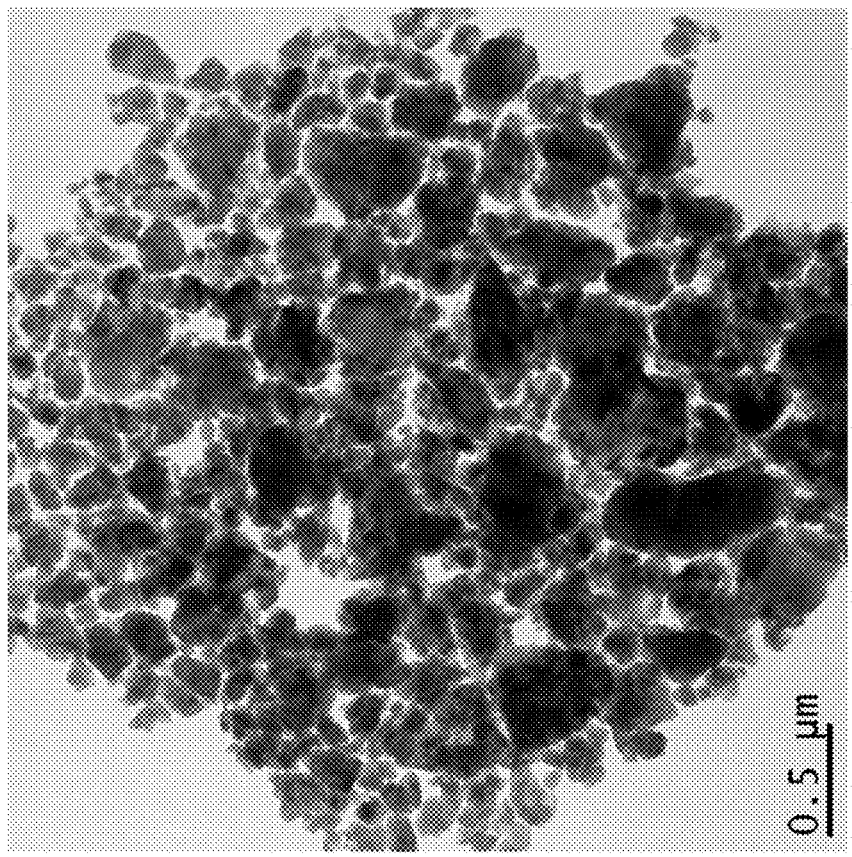
FIG. 4 is a TEM image of the herein disclosed product.

While specific embodiments are illustrated in the figures, with the understanding that the disclosure is intended to be illustrative, these embodiments are not intended to limit the invention described and illustrated herein.

DETAILED DESCRIPTION

Objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Herein, the use of the word "a" or "an" when used in conjunction with the term "comprising" in the claims and/or the specification may mean "one," but it is also consistent with the meaning of "one or more," "at least one," and "one or more than one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

Herein are provided processes for and the products of the mechanochemical functionalization of silicon surfaces by an alkane. Preferably, the mechanochemical functionalization of nanocrystalline silicon surfaces by an alkane. As used herein, mechanochemical means chemical processes initiated by the physical (mechanical) breakage of bonds, in some examples the physical breakage yields radicals that can recombine or carry out other reactions. As used herein nanocrystalline, nanocrystals, and nanoparticles refer to materials, crystals, or particles having dimensions on a nanometer scale, as crystal domains are a feature of this disclosure, crystal domains in nanocrystalline material, nanocrystals, and nanoparticles can have dimensions up to the dimensions of the respective material, crystal, or particles. When a crystal domain is on the same order as, for example, a nanocrystal, then the nanocrystal is single-crystalline.

In a first embodiment, the mechanochemically functionalizing silicon nanoparticles with an alkane includes repeatedly applying sufficient shear forces to silicon metal in the presence of an alkane. Herein, the sufficiency of the shear forces are determined by the reduction in the size of the silicon metal, that is, the mechanical size reduction in the silicon metal in the presence of the alkane. In one instance, a sufficient shear force is a shear force that mechanically shears single crystalline silicon. In another instance, a sufficient shear force is a shear force that mechanically shears polycrystalline silicon. The silicon is thereby mechanochemically functionalized and an alkyl-functionalization is provided on the surface of the silicon. The process further includes continuing to apply the shear forces to the silicon in the presence of the alkane until the silicon metal is reduced to a plurality of functionalized silicon nanoparticles.

In one instance, the applied forces are impact and shear forces. As used herein, impact and shear forces differ in the symmetry of the force as applied to a solid. Impact or compressive force is analogous to indentation or collision between the solid and the object applying the force. That is, the impact force is typically a compressive force applied to the material and the mechanical breakage of the material propagates via a cleavage plane (in Si this it typically along a (111) plane). In one instance, the impact force is the aligned forces of two external bodies acting on the material. Alternatively, the shear force is the unaligned forces which separate the material into different parts in inverse directions. Importantly, this embodiment fails to provide the functionalization of the silicon nanoparticles if the silicon metal is reduced in size by impact forces alone.

In another instance, the mechanochemical functionalization of the silicon includes shearing the silicon metal to expose silicon radicals on a shear surface and then reacting the silicon radicals with the alkane. Preferably, the silicon is sheared to expose a shear plane that includes silicon radicals. Then, prior to the reorganization of the silicon surface or other reactions, the silicon radicals react with the alkane. In one example, a silicon radical reacts with the alkane by cleaving a H—C and extracting a hydrogen radical from the alkane chain, thereby forming a silicon-hydride and leaving a carbon radical. This carbon radical can then react with a different silicon radical thereby providing alkane-functionalization of the silicon surface. In another example, the silicon radical reacts with the alkane by cleaving a C—C bond and forming a silicon alkyl functionalization and leaving a carbon radical that, then, can react with a second silicon radical. In another example, the shearing of the silicon metal provides a shear plane that is oriented between the (113) and (114) planes, that is, the shear plane is inclined relative to the silicon (111) plane. In still another example, the shear plane is not a silicon (111) plane. In yet another instance, the mechanochemical functionalization of the silicon includes fracturing the silicon metal to expose silicon radicals on a fracture surface. In one example, the fracturing of the silicon metal provides a fracture plane that is primarily aligned along the silicon (111) plane.

In still another instance, the silicon metal is reduced to a plurality of functionalized silicon nanoparticles having a $d_{90}$ of less than about 350 nm. Preferably, the functionalized silicon nanoparticles has a $d_{90}$ of less than about 300 nm. Even more preferably, the $d_{90}$ is less than about 250 nm.

Preferably, the shear forces are applied to the silicon metal in the presence of a liquid alkane. Notably, the application of shear forces adds heat to any system and the alkane can be solid at room temperature, only to melt as the shear forces add heat to the system. In another instance, the shear forces are applied to the silicon metal at a temperature above the melting point of the alkane. That is, any device carrying the silicon and the alkane can be heated to a temperature above the melting point of the alkane or held at a temperature above the melting point of the alkane. More preferably, the reaction is cooled to maintain a temperature that is above the melting point of the alkane, wherein the cooling and the heating by the application of the shear forces equilibrate to a selected temperature. In one example, the shear forces are applied at a temperature in the range of about 5-40° C., about 5-25° C., or about 5-20° C., with the necessary heating or cooling to maintain said temperature.

In another instance, the alkane can have a molecular formula of $C_xH_{2x+2}$ wherein x is in the range of 4 to about 25. Preferably, x is in the range of 5-20, more preferably in the range of 6-18, and even more preferably in the range of 6-12. Herein, the alkane can be liner (n-alkane), branched (single or multiple branches), cyclic, or a combination thereof. In one preferable example, the alkane is linear. In another preferable example, the alkane is branched. In still another instance, the alkane can carry a functional group wherein, preferably, the functional group does not include a heteroatom that is free of a direct bond to a hydrogen atom. Examples of functional groups include ethers, trialkyl-amines, imides, and tetraalkyl-silanes. Preferably, the functional groups are fully saturated and do not include any double bonds (e.g., excluding ketones, esters, and imides).

In yet another instance, the functionalized silicon nanoparticles are polycrystalline silicon nanocrystals. As used herein, a polycrystalline silicon nanocrystal is a discrete silicon nanocrystal that has more than one crystal domain. The domains can be of the same crystal structure and display discontinuous domains, or the domains can be of different crystal structures. In one example, the domains are all diamond-cubic silicon (e.g., having a lattice constant of 5.431 Å). In another example, the domains include a diamond-cubic silicon and a diamond-hexagonal silicon. In still another example, the domains include a diamond-cubic silicon and amorphous silicon. In yet still another example, the domains include a diamond-cubic silicon, a diamond-hexagonal silicon, and amorphous silicon.

Another embodiment is a process that includes repeatedly applying sufficient shear forces to silicon metal in the presence of an admixture of an alkane and an alkene thereby mechanochemically functionalizing the silicon and providing a functionalization on the surface of the silicon. In this embodiment, the shear forces are applied to the silicon in the presence of the alkane and the alkene until the silicon metal is reduced to a plurality of functionalized silicon nanoparticles. In one instance, the functionalization on the silicon surface is an admixture of an alkane-functionalization (derived from the alkane) and an alkene-functionalization (derived from the alkene).

In another instance, the alkane can have a molecular formula of $C_xH_{2x+2}$ wherein x is in the range of 4 to about 25. Preferably, x is in the range of 5-20, more preferably in the range of 6-18, and even more preferably in the range of 6-12. Herein, the alkane can be liner (n-alkane), branched (single or multiple branches), cyclic, or a combination thereof. In one preferable example, the alkane is linear. In another preferable example, the alkane is branched.

In still another instance, the alkene can have a molecular formula of $C_xH_{2x}$ wherein x is in the range of 5 to about 25. Preferably, x is in the range of 6-20, more preferably in the range of 6-18, and even more preferably in the range of 6-12. Herein, the alkene can be liner (n-alkene), branched (single or multiple branches), cyclic, or a combination thereof. In one preferable example, the alkene is linear. In another preferable example, the alkene is branched.

In yet another instance, the alkene can include a heteroatom functionality. Preferably, the heteroatom functionality is selected from an alcohol and an amine. In other examples, the heteroatom functionality can be selected from an alcohol, an aldehyde, a ketone, a carboxylate, an amine, an imide, a nitrile, a cyanate, an isocyanate, a thiocyanate, an isothiocyanate, an amide, a silyl, or a mixture thereof.

In still yet another instance, the functionalized silicon nanoparticles are polycrystalline silicon nanocrystals. As used herein, a polycrystalline silicon nanocrystal is a discrete silicon nanocrystal that has more than one crystal domain. The domains can be of the same crystal structure and display discontinuous domains, or the domains can be of different crystal structures. In one example, the domains are all diamond-cubic silicon (e.g., having a lattice constant of 5.431 Å). In another example, the domains include a diamond-cubic silicon and a diamond-hexagonal silicon. In still another example, the domains include a diamond-cubic silicon and amorphous silicon. In yet still another example, the domains include a diamond-cubic silicon, a diamond-hexagonal silicon, and amorphous silicon.

Still another embodiment is a process that includes shearing silicon metal and exposing a silicon surface having a Miller index other than a (111) plane or a (100) plane. Notably, the impact fracture of silicon metal (silicon crystal) by, for example, ball milling or grinding, predominately provides a silicon surface having a (111) Miller index. In part, this is driven by the fracture propagation in the silicon lattice being preferential in the (111) plane. Herein, shear forces are applied to the silicon surface and these forces provide shear propagation that is inclined relative to the (111) plane. Accordingly, the shearing of the silicon metal exposes silicon surfaces (shear surfaces or shear planes) that are inclined relative to the (111) plane. In one instance, the exposed silicon surface is oriented between the (113) and (114) planes. The exposed silicon surface can have other Miller indices, and preferentially have a plurality of exposed silicon surface that each have their own Miller indices. In one preferred instance, the silicon metal has a substantial portion that exists in a diamond-cubic crystal structure. Preferably, at least 10 atom %, 20 atom %, 25 atom %, 30 atom %, 35 atom %, 40 atom %, 45 atom %, 50 atom %, 55 atom %, 60 atom %, 65 atom %, 70 atom %, 75 atom %, 80 atom %, 85 atom %, 90 atom %, or 95 atom % of the silicon metal has a diamond-cubic crystal structure. Notably, the silicon metal can be single crystalline or can be polycrystalline. Additionally, the silicon metal can include alloying elements as long as the crystal structure maintains a substantial portion of diamond-cubic structure.

As a product of the shearing, the exposed silicon surface will carry at least one silicon radical. That is, the silicon metal that makes up the silicon surface will include at least one silicon radical, preferably, the silicon surface will carry a plurality of silicon radicals. More preferably, the as herein provided silicon radical is of sufficient energy to react with an alkane. That is, the silicon radical has sufficient energy to break a H—C or a C—C bond of an alkane.

This process further includes mechanochemically functionalizing the silicon surface by reacting the silicon radical with an organic coating agent. The reaction with the organic coating agent, preferably, covalently bonds the organic coating agent to the silicon surface (e.g., though a Si—C sigma bond).

In one instance, the organic coating agent is selected from an alkane, an alkene, an alkyne, an arene, an alkyl halide, an aryl halide, an aldehyde, a ketone, an ester, an amide, an amine, and a nitrile. In another instance, the organic coating agent is an admixture of at least two different compounds, each individually selected from an alkane, an alkene, an alkyne, an arene, an alkyl halide, an aryl halide, an aldehyde, a ketone, an ester, an amide, an amine, and a nitrile. Herein, the general classifications of the organic coatings agents further include combinations thereof. For example, the alkene and the alkyl halide classifications, each, include 8-chloro-octene. In one instance, the organic coating agent includes an alkane. In another instance, the organic coating agent consists essentially of an alkane. In yet another instance, the organic coating agent includes an alkene, an alkyne, or an aryl. In yet still another instance, the organic coating agent is free of a hydroxyl (—OH) functionality, i.e. the organic coating agent is preferably free of any alcohol. In another instance, the organic coating agent is free of hydroxyl and ether functionalities. In still yet another instance, the organic coating agent is free of any functionality that includes an oxygen atom.

Furthermore, the reaction of the silicon radical with the organic coating agent provides an organic radical (e.g., by extraction of a hydrogen atom for the organic coating agent, by the cleavage of a C—C bond in the organic coating agent, or by the reaction of an unsaturated functionality, for example an alkene, and the migration of the radical to a position on the organic coating agent). The organic radical, either carried on the silicon surface or within a reaction solution, is preferably, thereafter, quenched. The quenching can be, for example, by the reaction with other reagents within the reaction solution (e.g., by hydride extraction from another moiety) or by further reaction with the silicon surface.

Preferably, the silicon metal is repeatedly (e.g., continuously) sheared in the presence the organic coating agent until the silicon metal is reduced to a plurality of functionalized silicon nanoparticles. Herein, the functionalized silicon nanoparticles include an organic coating functionality covalently bound to the silicon surface. As used herein, the organic coating functionality is understood to include the radical addition of the organic coating agent to the silicon surface and the quenching of any resultant organic radical and/or a portion of the organic coating agent bound to the silicon surface (e.g., by the radical reaction of the organic coating agent with the silicon surface or by the addition of an organic radical with a silicon radical). Preferably, the plurality of functionalized silicon nanoparticles having a $d_{90}$ of less than about 350 nm, less than about 300 nm, or, more preferably, less than about 250 nm.

Yet another embodiment is a material that includes a plurality of silicon nanoparticles each carrying an alkyl-functionalization derived from an alkane. As used herein, the alkyl-functionalization can have a molecular formula of $C_xH_{2x+1}$ (wherein the alkane has a molecular formula of $C_xH_{2x+2}$) wherein x is in the range of 4 to about 25. Preferably, x is in the range of 5-20, more preferably in the range of 6-18, and even more preferably in the range of 5-12 or 6-12. Herein, the alkyl-functionalization can be liner, branched (single or multiple branches), cyclic, or a combination thereof. In one preferable example, the alkyl-functionalization is linear. In another preferable example, the alkyl-functionalization is branched. Still further, the alkyl-functionalization can have a non-specific chain length and orientation on the silicon surface. That is, the alkyl-functionalization can have a molecular formula of $C_xH_{2x+1}$ where x is not a single integer but is a range of integers from 1 to about 25 in those examples where the alkane had a molecular formula wherein x ranged up to 25. In instances wherein the silicon nanoparticles carry alkyl-functionalizations, each silicon nanoparticle can further carry a hydride functionalization (e.g., the silicon surface carries both alkyl and hydride groups bound to silicon atoms).

In one instance, the silicon nanoparticles include polycrystalline silicon nanocrystals. As used herein, a polycrystalline silicon nanocrystal is a discrete silicon nanocrystal that has more than one crystal domain. The domains can be of the same crystal structure and display discontinuous domains, or the domains can be of different crystal structures. In another instance, the silicon nanoparticles include silicon nanocrystals having dislocated diamond-cubic crystal structures. In still another instance, the silicon nanoparticles include silicon nanocrystals having diamond-cubic and diamond-hexagonal crystal structures. In still yet another instance, the silicon nanoparticles include silicon nanocrystals each having a plurality of crystal domains.

In another instance, the plurality of silicon nanoparticles has a $d_{90}$ of less than about 350 nm. Herein, the $d_{90}$ is the size distribution of the nanoparticles wherein for $d_{90}$ 90% of the particles have a size smaller than the represented value. Herein, the $d_{90}$ can be or be less than about 350 nm, 300 nm, 250 nm, or 200 nm.

In still another instance, each silicon nanoparticle further carries a functionalization derived from an alkene. Typically, the functionalization derived from an alkene has the same molecular formula as the alkene, for example a functionalization derived from octene ($C_8H_{16}$) bridges two neighboring silicon atoms on the surface and the functionalization has the formula $C_8H_{16}$. The functionalization derived from the alkene can have a molecular formula of $C_xH_2x$ wherein x is in the range of 5 to about 25. Preferably, x is in the range of 6-20, more preferably in the range of 6-18, and even more preferably in the range of 6-12. Herein, the functionalization derived from the alkene can be liner, branched (single or multiple branches), cyclic, or a combination thereof. In one preferable example, the functionalization derived from the alkene is linear. In another preferable example, the functionalization derived from the alkene is branched. In yet another instance, the functionalization derived from the alkene can include a heteroatom functionality. Preferably, the heteroatom functionality is selected from an alcohol and an amine. In other examples, the heteroatom functionality can be selected from an alcohol, an aldehyde, a ketone, a carboxylate, an amine, an imide, a nitrile, a cyanate, an isocyanate, a thiocyanate, an isothiocyanate, an amide, a silyl, or a mixture thereof.

In still yet another instance, each silicon nanoparticle further carries a functionalization derived from an alkyne. Typically, the functionalization derived from an alkyne has the same molecular formula as the alkyne, for example a functionalization derived from octyne ($C_8H_{14}$) bridges two neighboring silicon atoms on the surface and the functionalization has the formula $C_8H_{14}$. The functionalization derived from the alkyne can have a molecular formula of $C_xH_2x_{-2}$ wherein x is in the range of 5 to about 25. Preferably, x is in the range of 6-20, more preferably in the range of 6-18, and even more preferably in the range of 6-12. Herein, the functionalization derived from the alkyne can be liner, branched (single or multiple branches), cyclic, or a combination thereof. In one preferable example, the functionalization derived from the alkyne is linear. In another preferable example, the functionalization derived from the alkyne is branched. In yet another instance, the functionalization derived from the alkyne can include a heteroatom functionality. Preferably, the heteroatom functionality is selected from an alcohol and an amine. In other examples, the heteroatom functionality can be selected from an alcohol, an aldehyde, a ketone, a carboxylate, an amine, an imide, a nitrile, a cyanate, an isocyanate, a thiocyanate, an isothiocyanate, an amide, a silyl, or a mixture thereof.

Herein, shear force or shear forces can be applied to the silicon metal by the application of a mill, mixer, or grinder that is capable of the high shearing mixing/milling of the silicon metal. Mechanical shearing methods may employ homogenizers, extruders, injection molding machines, roller blade mixers, Banbury® type mixers, Brabender® type mixers, pin-mixers, rotor/stator mixers, and the like. In one instance, shearing can be achieved by introducing the silicon and alkane at one end of an extruder (single or double screw) and receiving the sheared material at the other end of the extruder. The temperature of the materials entering the extruder, the temperature of the extruder, the concentration of materials added to the extruder, the amount of solvent (alkane) added to the extruder, the length of the extruder, residence time of the materials in the extruder, and the design of the extruder (single screw, twin screw, number of flights per unit length, channel depth, flight clearance, mixing zone, etc.) are several variables which control the amount of shear applied to the materials. In another instance, shearing can be achieved by passing an admixture of the silicon metal and alkane through a rotor-stator (e.g., a rotor-stator mixer, a rotor-stator homogenizer, or a rotor-stator mill). The rotor-stator can employ a pin-mill design, a conical pass designs, disk design, or the like. In some instances, the rotor-stator can include a bead mill. Notably, the application of the shear force(s) can be accomplished as a batch, a semi-batch, or a circulating flow, or a continuous flow process.

As used herein, the processes and products are described relative to silicon metal. In one example, the silicon metal is analytically pure silicon, for example, single crystal silicon (e.g., platters) used in the semiconductor/computer industry. In another example, the silicon metal is recycle or scrap from the semiconductor or solar industries. In still another example, the silicon metal is a silicon alloy. A silicon alloy can be a binary alloy (silicon plus one alloying element), can be a tertiary alloy, or can include a plurality of alloying elements. The silicon alloy is understood to be a majority silicon. A majority silicon particle means that the metal has a weight percentage that is greater than about 50% (50 wt. %) silicon, preferably greater than about 60 wt. %, 70 wt. %, 80 wt. %, 90 wt. %, or 95 wt. % silicon; these can include silicon alloys that comprise silicon and at least one alloying element. The alloying element can be, for example, an alkali metal, an alkaline-earth metal, a Group 13 to 16 element, a transition element, a rare earth element, or a combination thereof, but not Si. The alloying element can be, e.g., Li, Na, Mg, Ca, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, B, Al, Ga, In, Ge, Sn, P, As, Sb, Bi, S, Se, Te, or a combination thereof. In one instance, the alloying element can be lithium, magnesium, aluminum, titanium, vanadium, chromium, manganese, iron, cobalt, nickel, copper, or a mixture thereof. In another instance, the silicon alloy can be selected from SiTiNi, SiAlMn, SiAlFe, SiFeCu, SiCuMn, SiMgAl, SiMgCu, or a combination thereof.

In still another example, the herein described processes and products can utilize germanium and/or indium, without or without silicon. Accordingly, the processes and products describe above can be include Ge or In in replacement of the Si. Still further, the processes and products can utilize alloys of Ge or In.

EXAMPLES

Non-Shear Example

Silicon metal was processed for 12 hours in a high-energy ball mill in accordance to the descriptions provided in U.S. Pat. No. 7,883,995. The non-shear product was analyzed by FTIR, SEM, and TEM. The non-shear product showed no alkane functionalization of the silicon metal.

High-Shear Example

A silicon metal feed stock was prepared from silicon wafer (single crystal) by pre-crushing and sieving the silicon metal to less than 250 μm. Then 250 g of the sieved silicon metal and about 1000 g of n-hexane were admixed and the silicon continuously suspended in the n-hexane by application of a paddle-type (non-shear) mixer. The suspension was recirculated through a rotor-stator mill for 3-6 hours. Aliquots were removed about every 30 min and the particle size was determined. After the silicon is reduced to nanoparticles, the slurry was removed from the rotor-stator system and the hexane evaporated. The resulting product was processed to provide a free-flowing powder and then dried in a vacuum oven. This high-shear product was analyzed by FTIR, SEM, and TEM. The high-shear product showed alkane functionalization on the silicon and a different morphology by SEM and TEM.

While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A process of mechanochemically functionalizing silicon nanoparticles with an alkane, comprising:
   shearing silicon metal in the presence of an alkane by applying shear forces to the silicon metal to expose a sheared silicon surface, the alkane having a molecular formula of $C_xH_{2x+2}$ where x is in the range of 4 to about 25,
   forming an alkyl-functionalization on the sheared silicon surface; and
   continuing to shear the silicon metal in the presence of the alkane until the silicon metal is reduced to a plurality of functionalized silicon nanoparticles.

2. The process of claim 1, wherein shearing the silicon metal exposes silicon radicals on the sheared silicon surface, the process then including reacting the silicon radicals with the alkane to provide the alkyl-functionalization.

3. The process of claim 2, further comprising fracturing the silicon metal to expose silicon radicals on a fractured silicon surface.

4. The process of claim 1, wherein the plurality of functionalized silicon nanoparticles have a $d_{90}$ of less than about 350 nm.

5. A process comprising:
   repeatedly applying sufficient shear forces to silicon metal in the presence of an admixture of an alkane and an alkene thereby mechanochemically functionalizing the silicon and providing a functionalization on the surface of the silicon, the alkane having a molecular formula of $C_xH_{2x+2}$ where x is in the range of 4 to about 25, the alkene having a molecular formula of $C_xH_{2x}$ where x is in the range of 5 to about 25; and
   continuing to apply the shear forces to the silicon in the presence of the alkane and the alkene until the silicon metal is reduced to a plurality of functionalized silicon nanoparticles.

6. The process of claim 5, wherein the functionalization on the silicon surface is an admixture of an alkane-functionalization and an alkene-functionalization.

7. The process of claim 5, wherein the functionalized silicon nanoparticles are polycrystalline silicon nanocrystals.

8. A process comprising:
   shearing silicon metal thereby exposing a silicon surface having a Miller index other than a (111) plane or a (100) plane, the silicon surface carrying at least one silicon radical; where the silicon radical is of sufficient energy to react with an alkane;
   mechanochemically functionalizing the silicon surface with a Si—C sigma bond.

9. The process of claim 8, wherein at least 25 atom % of the silicon metal has a diamond-cubic crystal structure.

10. The process of claim 8, wherein mechanochemically functionalizing the silicon surface with a Si—C sigma bond include reacting the silicon radical with an organic coating agent and forming an organic radical, thereafter quenching the organic radical.

11. The process of claim 8, wherein the process comprises:
    repeatedly shearing the silicon metal, thereby repeatedly exposing a plurality of silicon radicals on a plurality of silicon surfaces and mechanochemically functionalizing the silicon surfaces with Si—C sigma bonds, and thereby reducing the silicon metal to a plurality of functionalized silicon nanoparticles.

12. The process of claim 11, wherein mechanochemically functionalizing the silicon surfaces with Si—C sigma bonds includes reacting the silicon radicals with an alkane having a molecular formula of $C_xH_{2x+2}$ where x is in the range of 4 to about 25.

13. The process of claim 12, wherein mechanochemically functionalizing the silicon surfaces with Si—C sigma bonds consists essentially of reacting the silicon radicals with the alkane.

14. The process of claim 11, wherein the plurality of functionalized silicon nanoparticles having a $d_{90}$ of less than about 350 nm.

15. The process of claim 14, wherein the $d_{90}$ is less than about 300 nm.

16. The process of claim 15, wherein the $d_{90}$ is less than about 250 nm.

* * * * *